United States Patent
Schmeling et al.

(10) Patent No.: US 10,572,630 B1
(45) Date of Patent: Feb. 25, 2020

(54) REFILL PRESCRIPTION BY CALENDAR REMINDER

(71) Applicant: WALGREEN CO., Deerfield, IL (US)

(72) Inventors: Todd Schmeling, Gurnee, IL (US); Kartik Subramanian, Chicago, IL (US)

(73) Assignee: WALGREEN CO., Deerfield, IL (US)

( * ) Notice: Subject to any disclaimer, the term of this patent is extended or adjusted under 35 U.S.C. 154(b) by 391 days.

(21) Appl. No.: 15/487,718

(22) Filed: Apr. 14, 2017

(51) Int. Cl.
*G06F 19/00* (2018.01)
*G06Q 10/10* (2012.01)

(52) U.S. Cl.
CPC ........ *G06F 19/3456* (2013.01); *G06F 19/328* (2013.01); *G06Q 10/1093* (2013.01)

(58) Field of Classification Search
None
See application file for complete search history.

(56) References Cited

U.S. PATENT DOCUMENTS

| | | | | |
|---|---|---|---|---|
| 4,766,542 A | * | 8/1988 | Pilarczyk | G06F 19/3456 705/3 |
| 5,970,462 A | * | 10/1999 | Reichert | G06F 19/3456 705/2 |
| 10,210,311 B1 | * | 2/2019 | Taneja | G16H 40/67 |
| 2002/0143580 A1 | * | 10/2002 | Bristol | G06Q 50/22 705/2 |
| 2003/0120516 A1 | * | 6/2003 | Perednia | G06F 19/3418 705/3 |
| 2004/0243588 A1 | * | 12/2004 | Tanner | G06F 16/2471 |
| 2005/0010446 A1 | * | 1/2005 | Lash | G06Q 10/10 705/2 |
| 2005/0256737 A1 | * | 11/2005 | Liu | G06Q 50/22 705/2 |
| 2007/0061169 A1 | * | 3/2007 | Lorsch | G06Q 50/22 705/3 |
| 2007/0100662 A1 | * | 5/2007 | Suwalski | G06Q 10/06 705/2 |
| 2007/0198296 A1 | * | 8/2007 | Pellinat | G06F 19/3418 705/2 |

(Continued)

OTHER PUBLICATIONS

U.S. Appl. No. 13/738,556, filed Jan. 10, 2013.

*Primary Examiner* — Michael Tomaszewski
(74) *Attorney, Agent, or Firm* — Marshall, Gerstein & Borun LLP; Randall G. Rueth

(57) ABSTRACT

The method and system may provide a service that allows a customer to order refills of prescription medications in a quick and hassle-free manner from a remote location using a virtual calendar on a computer or mobile device. The system identifies prescription medications eligible for refill by a customer on a particular date and transmits a calendar event to the customer. The calendar event includes a refill reminder identifier corresponding to the prescription medications eligible for refill. The customer replies to the calendar event that includes the refill reminder identifier. The system then receives the reply electronic communication from the customer and validates the refill reminder identifier associated with the reply electronic communication. Accordingly, the system retrieves prescription numbers associated with the refill reminder identifier and transmits the retrieved prescription numbers for filling and dispensing the prescription medications.

20 Claims, 8 Drawing Sheets

(56) References Cited

U.S. PATENT DOCUMENTS

| | | | |
|---|---|---|---|
| 2008/0059228 A1* | 3/2008 | Bossi | G06F 19/3418 705/2 |
| 2008/0077439 A1* | 3/2008 | Guion | G06Q 50/22 705/2 |
| 2008/0281165 A1* | 11/2008 | Rai | A61B 5/0002 600/300 |
| 2011/0307265 A1* | 12/2011 | Bannis | G06Q 50/22 705/2 |
| 2013/0191145 A1* | 7/2013 | Nudd | G06Q 10/063118 705/2 |
| 2013/0218595 A1* | 8/2013 | Burkett | G06Q 40/00 705/3 |
| 2015/0058035 A1* | 2/2015 | Ayshford | G06F 19/3456 705/2 |
| 2015/0161351 A1* | 6/2015 | Scalpati | G06F 19/3456 705/2 |
| 2017/0053093 A1* | 2/2017 | Humphreys | G06F 19/328 |
| 2018/0150611 A1* | 5/2018 | Hasan | G06F 21/6245 |

\* cited by examiner

REFILL PRESCRIPTION BY CALENDAR REMINDER

TECHNICAL FIELD

The present disclosure generally relates to a system and method for refilling prescription medications and, more particularly, to providing calendar events allowing a customer to order one or more prescription refills directly from the customer's virtual calendar, in an expeditious manner, and preferably without entering login information typically required of online systems.

BACKGROUND

While some medications prescribed to patients may be taken only for a brief period of time, other medications may be taken for extended periods of time. For convenience, when a doctor prescribes a medication that will be taken over an extended period, the doctor may write the prescription such that a pharmacy can refill the prescription one or more times without requiring renewed authorization from the doctor (i.e., without requiring a new prescription). When a patient runs out of the prescribed medication (or slightly before), the patient may contact the pharmacy at which the prescription was originally filled and request a refill, if there are any refills remaining. Of course, if no refills remain, a pharmacist at the pharmacy may contact the doctor to request a new prescription for the same medication without involving the patient.

Pharmacies have implemented internet-based interfaces (e.g., web sites) through which a patient could request a refill. To access the web pages through which prescription refills may be requested, a patient must be logged into a user profile. Generally, though not always, the user profile is associated with only one person, and the user can order refills only of the prescriptions associated with his profile. Some systems allow for a profile to be associated with multiple people (e.g., family members, patients in the charge of a caregiver, etc.), but this requires additional configuration steps that must be performed in advance, such as sending and responding to requests for permission, that often must be coordinated between multiple people.

In any event, the systems currently in place require a user who wishes to order a prescription refill to log into the system. For example, the Health Insurance Portability and Accountability Act (HIPAA) sets certain privacy and security standards for protected health information (PHI) transmitted by electronic media. Such standards may require a user name and password to authenticate a user viewing prescription numbers. For some patients, remembering the user name or password may be difficult and, if the patient does not have access to the information, the login requirement may prevent access to the system entirely. Even in cases where the patient knows (or has access to) the user name and password, entering the login information may be an impediment, especially for users attempting to order refills through a mobile device, many of which have input mechanisms that are difficult or, at least, inconvenient to use. Further, logging into the system requires access to a web browser, which may not be readily available to the customer.

SUMMARY

To refill a customer's prescriptions, a prescription refill system may identify medications (also referred to herein as "drugs") having the same refill date that are prescribed to the customer or a patient who designates the customer to pick up prescriptions on behalf of the patient. Each prescription medication or drug may have a corresponding prescription number. The prescription refill system may then generate a refill reminder identifier that uniquely identifies each of the prescription medications (e.g., by prescription number) for the refill date.

A calendar event is generated for the customer for the refill date and transmitted to the customer's client device for display on a virtual calendar. In this manner, the customer is reminded to refill prescriptions on her virtual calendar on the date that the prescriptions are eligible for refill. The calendar event may include the refill reminder identifier, such that the customer may order refills for each of the corresponding prescription medications directly from the virtual calendar. For example, by replying to the calendar event (e.g., via a reply email, short message service (SMS) text message, etc.), the prescription refill system may receive the refill reminder identifier in the reply communication (e.g., in the subject line of the reply email). The refill reminder identifier may then be used to retrieve the corresponding prescription numbers for the prescription medications to generate a refill order for filling and dispensing the prescription medications to the customer.

In this manner, the present embodiments advantageously allow the prescription refill system to comply with HIPAA requirements without requiring the customer to enter login information. This also eliminates the need for a web browser which may not be accessible to the customer in some scenarios. Instead, a customer may refill prescriptions directly from her virtual calendar. In this manner, the customer's refill dates are displayed in a user-friendly manner to properly remind the customer when prescriptions are eligible for a refill. Therefore, the customer does not need to search through earlier emails or a message history to find the refill reminder.

Furthermore, by assigning a refill reminder identifier to uniquely identify several of the customer's prescriptions, the present embodiments advantageously reduce the amount of information transmitted over the network by transmitting a single refill reminder identifier as opposed to separate identifiers for each prescription. Additionally, the prescription refill system may retrieve each of the prescriptions corresponding to the refill reminder identifier in a single search. The prescription refill system does not have to search a database several times to obtain each of the customer's prescriptions.

In one embodiment, a method of providing a refill order via a calendar reminder includes identifying one or more prescription drugs eligible for refill for a user on a particular refill date, generating a refill reminder identifier associated with the one or more prescription drugs for uniquely identifying each of the one or more prescription drugs, and transmitting, to a client device of the user, a calendar event to be displayed on a virtual calendar of the client device on the particular refill date, the calendar event including the refill reminder identifier. In response to transmitting the refill reminder identifier to the client device, the method includes receiving an electronic communication from the virtual calendar of the user, the electronic communication including the refill reminder identifier. Additionally, in response to receiving the electronic communication, the method includes obtaining an indicator for each of the one or more prescription drugs corresponding to the refill reminder identifier and providing the indicators for filling and dispensing the one or more prescription drugs to the user.

In another embodiment, a system for providing a refill order via a calendar reminder is provided. The system includes one or more processors, a communication network and a non-transitory computer-readable memory coupled to the one or more processors, and the communication network and storing instructions thereon. When executed by the one or more processors, the instructions cause the system to identify one or more prescription drugs eligible for refill for a user on a particular refill date, generate a refill reminder identifier associated with the one or more prescription drugs for uniquely identifying each of the one or more prescription drugs, and transmit, via the communication network to a client device of the user, a calendar event to be displayed on a virtual calendar of the client device on the particular refill date, the calendar event including the refill reminder identifier. In response to transmitting the refill reminder identifier to the client device, the instructions cause the system to receive, via the communication network, an electronic communication from the virtual calendar of the user, the electronic communication including the refill reminder identifier. Additionally, in response to receiving the electronic communication, the instructions cause the system to obtain an indicator for each of the one or more prescription drugs corresponding to the refill reminder identifier and provide the indicators for filling and dispensing the one or more prescription drugs to the user.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment of thereof. Further, wherever possible, the following description refers to the reference numerals included in the following figures, in which features depicted in multiple figures are designated with consistent reference numerals.

DETAILED DESCRIPTION

Figure 1A:
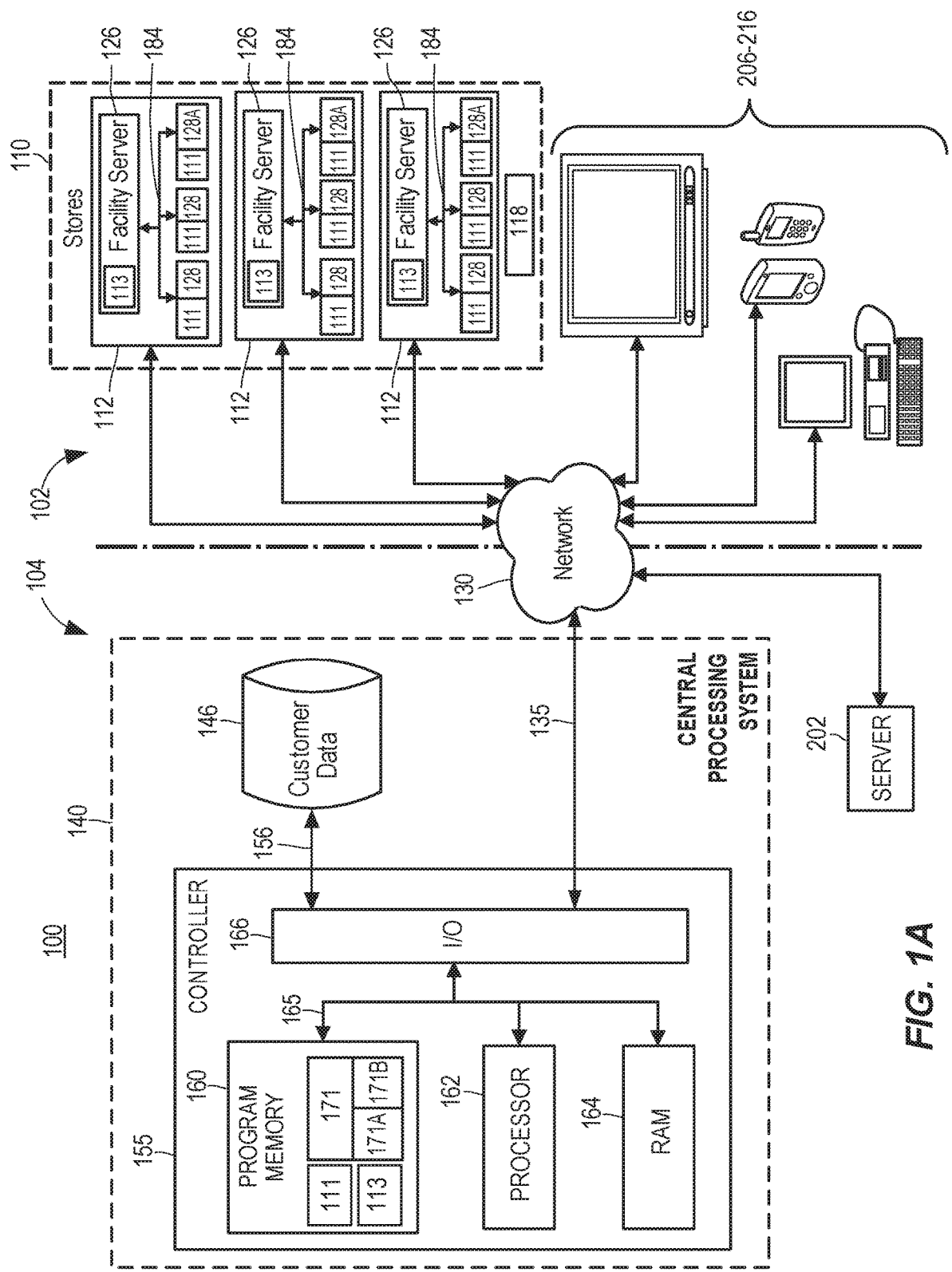
FIG. 1A illustrates a block diagram of a computer network and system on which an exemplary prescription refill system and method may operate in accordance with the described embodiments.

Although the following text sets forth a detailed description of numerous different embodiments, it should be understood that the legal scope of the description is defined by the words of the claims set forth at the end of this patent and equivalents. The detailed description is to be construed as exemplary only and does not describe every possible embodiment since describing every possible embodiment would be impractical. Numerous alternative embodiments could be implemented, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

Generally speaking, techniques for refilling a prescription via a refill reminder may be implemented in a client device, one or several network servers, or a system that includes a combination of these devices. However, for clarity, the examples below focus primarily on an embodiment in which a server creates a virtual calendar for a customer having calendar events on the dates on which the customer's prescription medications are eligible for refill. The server may provide a calendar subscription link to the customer's client device requesting the customer to subscribe to the virtual calendar to receive updates when current and subsequent prescriptions become eligible for refill. In response to receiving confirmation from the customer indicating the customer subscribed to the calendar, the server may provide calendar events to the customer's client device to be displayed via a virtual calendar application on the client device. The calendar events may include a refill reminder identifier for identifying the prescription medications eligible for refill on a corresponding refill date. The customer's client device may include user controls for responding to a calendar event via the virtual calendar application or a mail application. In response to receiving a reply to the calendar event that includes the refill reminder identifier, the server may provide prescription numbers for prescription medications corresponding to the refill reminder identifier for filling and dispensing the prescription medications.

FIG. 1A illustrates various aspects of an exemplary architecture implementing a prescription refill system 100. In particular, FIG. 1A illustrates a block diagram of the exemplary prescription refill system 100. The high-level architecture includes both hardware and software applications, as well as various data communications channels for communicating data between the various hardware and software components. The prescription refill system 100 may be roughly divided into front-end components 102 and back-end components 104. The front-end components 102 are primarily disposed within a retail network 110 including one or more pharmacies 112. The pharmacies 112 may be located, by way of example rather than limitation, in separate geographic locations from each other, including different areas of the same city, different cities, or even different states. The front-end components 102 comprise a number of pharmacy workstations 128. The pharmacy workstations 128 are local computers located in the various pharmacies 112 throughout the retail network 110 and executing various pharmacy management-related applications. Pharmacists, technicians, and other pharmacy personnel, referred to collectively herein simply as "pharmacists" (not shown), use the pharmacy workstations 128 to access customer information, enter new prescriptions, access insurance and payment information and so forth. Each of the pharmacies 112 may be, for example, an in-store retail pharmacy, an on-line pharmacy, a mail-order pharmacy, a long-term care pharmacy, a workplace/on-site pharmacy, or a specialty pharmacy. The retail network 110 may also include one or more warehouses or central-filling facilities 118. The warehouses or central-filling facilities 118 may distribute medications or retail products to the various retail pharmacies 112 in the retail network 110, or may distribute medications or retail products directly to customers. Client devices 206-216 (e.g., personal computers, cellular phones, smart phones, internet-enabled televisions, etc.) may be communicatively connected to the pharmacies 112 and to a system 140 through a digital network 130, as described below.

Those of ordinary skill in the art will recognize that the front-end components 102 could also comprise a plurality of facility servers 126 disposed at the plurality of pharmacies 112 instead of, or in addition to, a plurality of pharmacy workstations 128. Each of the pharmacies 112 may include one or more facility servers 126 that may facilitate communications between the workstations 128 of the pharmacies 112 via a digital network 130, and may store information for a plurality of customers/employees/accounts/etc. associated with each facility. Of course, a local digital network 184 may also operatively connect each of the workstations 128 to the facility server 126. Unless otherwise indicated, any discussion of the workstations 128 also refers to the facility servers 126, and vice versa. Moreover, environments other than the pharmacies 112 may employ the workstations 128 and the servers 126. As used herein, the term "pharmacy" refers to any of these environments (e.g., call centers, kiosks, Internet interface terminals, etc.) in addition to the retail pharmacies 112, etc. described above.

The front-end components 102 communicate with the back-end components 104 via the digital network 130. One or more of the front-end components 102 may be excluded from communication with the back-end components 104 by configuration or by limiting access due to security concerns. For example, the client devices 206-216 may be excluded from direct access to the back-end components 104. In some embodiments, the pharmacies 112 may communicate with the back-end components via the digital network 130. In other embodiments, the pharmacies 112 and client devices 206-216 may communicate with the back-end components 104 via the same digital network 130, but digital access rights, IP masking, and other network configurations may deny access to the client devices 206-216.

The digital network 130 may be a proprietary network, a secure public Internet, a virtual private network or some other type of network, such as dedicated access lines, plain ordinary telephone lines, satellite links, combinations of these, etc. Where the digital network 130 comprises the Internet, data communication may take place over the digital network 130 via an Internet communication protocol. In addition to one or more servers 202 (described below), the back-end components 104 include the central processing system 140 within a central processing facility, such as, for example, the central processing facility described in U.S. patent application Ser. No. 12/271,686 entitled "DISTRIBUTED PHARMACY PRESCRIPTION PROCESSING SYSTEM" the entire disclosure of which is incorporated by reference herein. Of course, the pharmacies 112 may be communicatively connected to different back-end components 104 having one or more functions or capabilities that are similar to the central processing system 140. The central processing system 140 may include one or more computer processors 162 adapted and configured to execute various software applications and components of the prescription refill system 100, in addition to other software applications. The central processing system 140 further includes a database 146. The database 146 is adapted to store data related to the operation of the prescription refill system 100 (e.g., user profile data including diagnoses, past healthcare product and medication purchases, prescription histories, associations between patients and customers, prescription medications eligible for refill, etc.) The central processing system 140 may access data stored in the database 146 when executing various functions and tasks associated with the operation of the prescription refill system 100.

Although FIG. 1A depicts the prescription refill system 100 as including the central processing system 140 in communication with three pharmacies 112, and various client devices 206-216 it should be understood that different numbers of processing systems, pharmacies, and devices may be utilized. For example, the digital network 130 (or other digital networks, not shown) may interconnect the central processing system 140 to a plurality of included central processing systems 140, hundreds of pharmacies 112, and thousands of client devices 206-216. According to the disclosed example, this configuration may provide several advantages, such as, for example, enabling near real-time uploads and downloads of information as well as periodic uploads and downloads of information. This provides for a primary backup of all the information generated in the electronic message refill reply process. Alternatively, some of the pharmacies 112 may store data locally on the facility server 126 and/or the workstations 128.

FIG. 1A also depicts one possible embodiment of the central processing system 140. The central processing system 140 may have a controller 155 operatively connected to the database 146 via a link 156 connected to an input/output (I/O) circuit 166. It should be noted that, while not shown, additional databases may be linked to the controller 155 in a known manner.

The controller 155 includes a program memory 160, the processor 162 (may be called a microcontroller or a microprocessor), a random-access memory (RAM) 164, and the input/output (I/O) circuit 166, all of which are interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM(s) 164 and the program memories 160 may be implemented as semiconductor memories, magnetically readable memories, and/or optically readable memories, for example. A link 135 may operatively connect the controller 155 to the digital network 130 through the I/O circuit 166.

The program memory 160 may also contain machine-readable instructions (i.e., software) 171, for execution by the processor 162. The software 171 may perform the various tasks associated with operation of the pharmacy or pharmacies, and may be a single module 171 or a plurality of modules 171A, 171B. While the software 171 is depicted in FIG. 1A as including two modules, 171A and 171B, the software 171 may include any number of modules accomplishing tasks related to pharmacy operation including, for example, receiving prescription orders, managing prescription workflow, etc. The central processing system 140 implements a server application 113 for providing data to a user interface application 111 operating on the workstations 128.

Figure 1B:
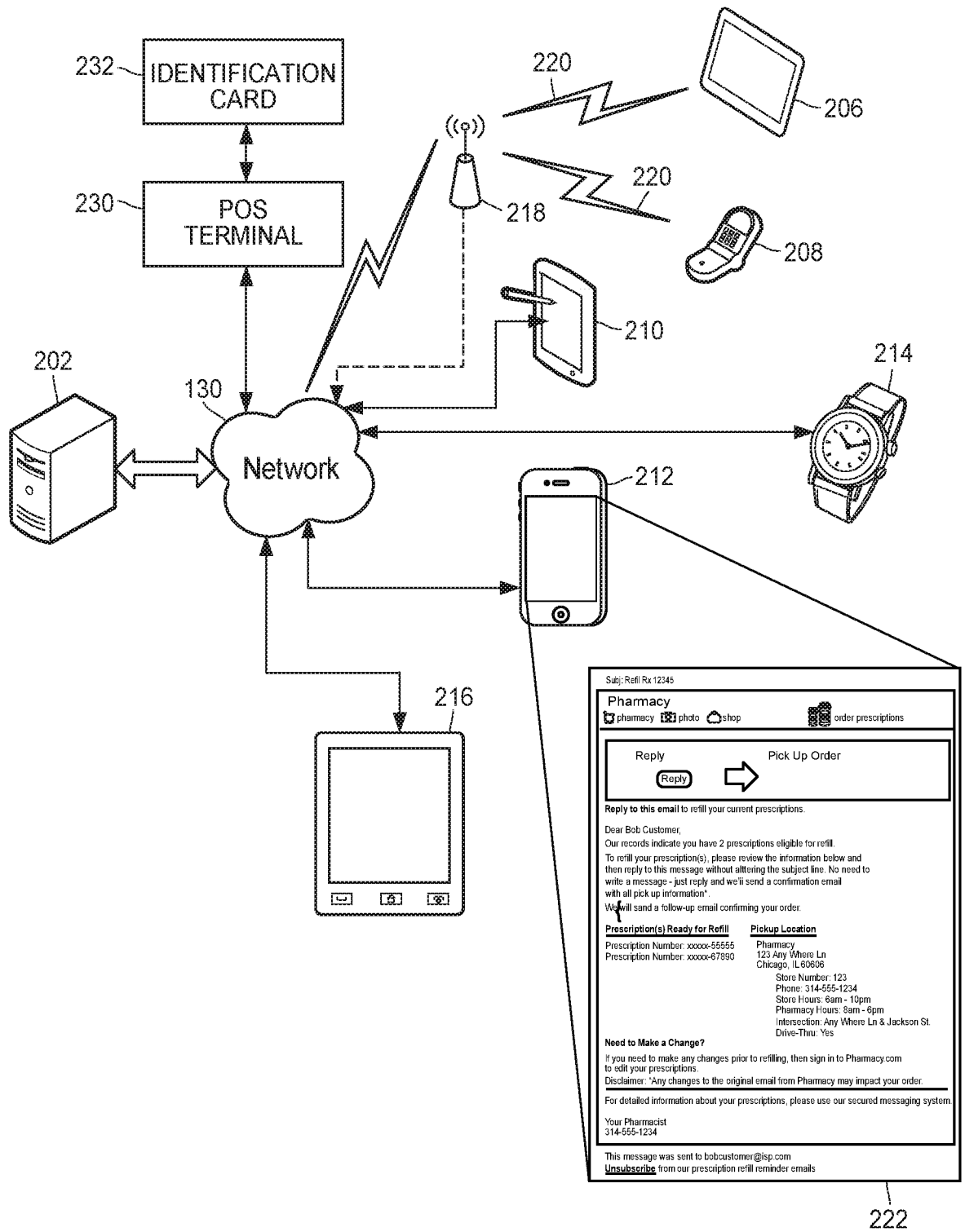
FIG. 1B illustrates client devices and associated equipment that may operate with a network and a server.

For purposes of implementing the prescription refill system 100, the user interacts with the server 202 and the pharmacy systems (e.g., the central processing system 140) via a client device 206-216 (e.g., mobile device application, web browser application, etc.), a specialized application, or a plurality of web pages. FIG. 1B depicts the server 202 connected via the network 130 to the client devices 206-216 through which a user may initiate and interact with the prescription refill system 100 (as shown in FIG. 1A). The client devices 206-216 may include, by way of example, a tablet computer 206, an internet-enabled cell phone 208, a personal digital assistant (PDA) 210, a mobile device smartphone 212 also referred to herein as a "mobile device," a watch or other wearable computer 214, a thin-client device 216, a laptop computer (not shown), a desktop computer (not shown), a portable media player (not shown), etc. Of course, any client device appropriately configured may interact with the prescription refill system 100. A thin-client device 216 is a client device that depends on a master computing device (e.g., a server, a mainframe computer, etc.) to which it is connected through a network interface. A thin-client device 216 may depend on the central processing system 140 to handle many functions that are performed locally by traditional computing systems (e.g., data storage and access, data processing). For example, a thin-client device 216 may merely act as a remote input/output device that accepts user input and transmits the input to the central processing system 140. Then, the central processing system 140 may process the input and transmit output as well as accessing or storing data as needed. Thus, the thin-client device 216 could be a more streamlined device, requiring only an input device (e.g., a touch-screen), an output device (e.g., a touch-screen), networking capability (e.g., a transmitter and receiver), and the necessary software to accept input, relay it to the server, and accept and display output. Of course, a thin-client device 216 may perform a larger number of processes locally and leave only a few functions (e.g., data persistence) for the central processing system 140 to perform.

The client devices 206-216 need not necessarily communicate with the network 130 via a wired connection. In some instances, the client devices 206-216 may communicate with the network 130 via wireless signals 220 and, in some instances, may communicate with the network 130 via an intervening wireless or wired device 218, which may be a wireless router, a wireless repeater, a base transceiver station of a mobile telephony provider, etc. Each of the client devices 206-216 may interact with the server 202 to receive web pages or server data from the server 202 and may display the web pages or server data via a virtual calendar application (described below). For example, the mobile device 212 may display a calendar event 222 of the virtual calendar application to the user, may receive an input from the user, and may interact with the server 202 depending on the type of user-specified input. It will be appreciated that although only one server 202 is depicted in FIG. 1B, multiple servers 202 may be provided for the purpose of distributing server load, serving different web pages, implementing different portions of the pharmacy web interface, etc. These multiple servers 202 may include a web server, an entity-specific server (e.g. an Apple® server, etc.), a server that is disposed in a retail or proprietary network, an independent third-party server that is not under the control of the entity, etc.

Figure 1C:
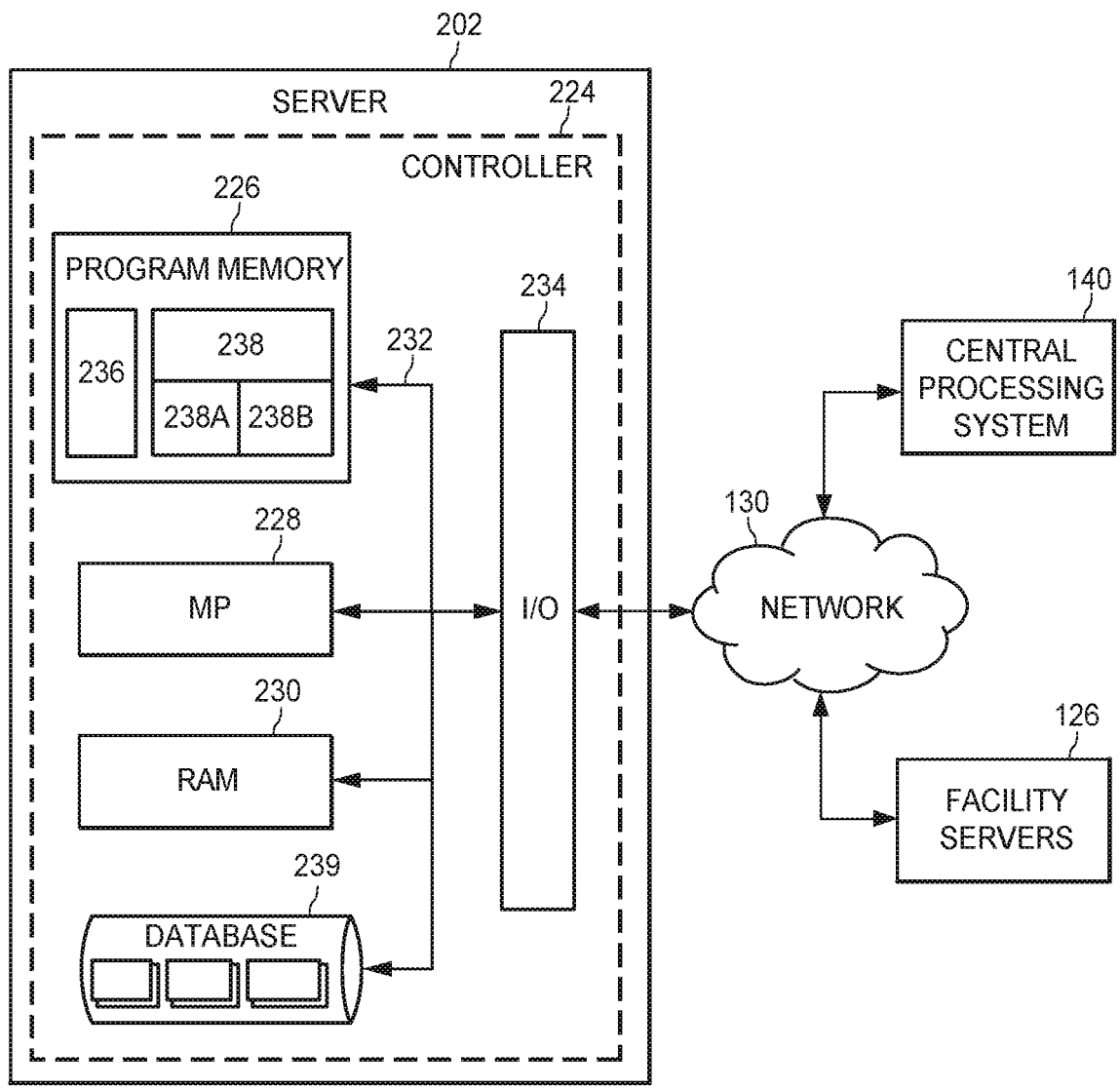
FIG. 1C illustrates a block diagram of an exemplary server.

Turning now to FIG. 1C, the server 202, like the facility server 126, includes a controller 224. Similar to the controllers 155 and 170, the controller 224 includes a program memory 226, a microcontroller or a microprocessor (MP) 228, a random-access memory (RAM) 230, and an input/output (I/O) circuit 234, all of which are interconnected via an address/data bus 232. In some embodiments, the controller 224 may also include, or otherwise be communicatively connected to, a database 239 or other data storage mechanism (e.g., one or more hard disk drives, optical storage drives, solid state storage devices, etc.). The database 239 may include data such as user profiles, product data, mobile device application data, web page templates and/or web pages, an email inbox (not shown) that stores and indexes received and sent emails, and other data necessary to interact with the user through the network 130. As discussed with reference to the controllers 155 and 170, it should be appreciated that although FIG. 1C depicts only one microprocessor 228, the controller 224 may include multiple microprocessors 228. Similarly, the memory of the controller 224 may include multiple RAMs 230 and multiple program memories 226. Although the FIG. 1C depicts the I/O circuit 234 as a single block, the I/O circuit 234 may include a number of different types of I/O circuits. The controller 224 may implement the RAM(s) 230 and the program memories 226 as semiconductor memories, magnetically readable memories, and/or optically readable memories, for example.

In addition to being connected through the network 130 to the client devices 206-216, as depicted in FIG. 1B, FIG. 1C illustrates that the server 202 may also be connected through the network 130 to the central processing system 140 and/or one or more facility servers 126. As described below, the connection of the server 202 to the central processing system 140 assists in facilitating some of the functionality of the prescription refill process. As a result, the server 202 may act as a routing or interfacing server between the plurality of client devices 206-216 and a destination server, namely, the central processing system 140. For example, the server 202 may be configured to communicate with the central processing system 140 and with the client device 206-216 via a multitude of protocols, such as packet-switched protocols, web services, web APIs, etc. The server 202 may also convert (if necessary) and route application data (not shown) to the appropriate server, such as the central processing system 140 for example. Additionally, the server 202 may act as the destination server and need not route any data from the client device 206-216.

As shown in FIG. 1C, the program memory 226 and/or the RAM 230 may store various applications for execution by the microprocessor 228. For example, a user-interface application 236 may provide a user interface to the server 202, which user interface may, for example, allow a network administrator to configure, troubleshoot, or test various aspects of the server's operation, or otherwise to access information thereon. A server application 238 operates to populate and transmit virtual calendar application data and web pages to the client devices 206-216, receive information from the user transmitted back to the server 202, and forward appropriate data to the central processing system 140 and the facility servers 126, as described below. Like the software 171 of FIGS. 1A and 1B, the server application 238 may be a single module 238 or a plurality of modules 238A, 238B. While the server application 238 is depicted in FIG. 1C as including two modules, 238A and 238B, the server application 238 may include any number of modules accomplishing tasks related to implantation of the server 202. By way of example, the module 238A may populate and transmit the virtual calendar application data and/or may receive and evaluate inputs from the user to receive a data access request, while the module 238B may communicate with one or more of the back end components 104 to fulfill a data access request.

Figure 1D:
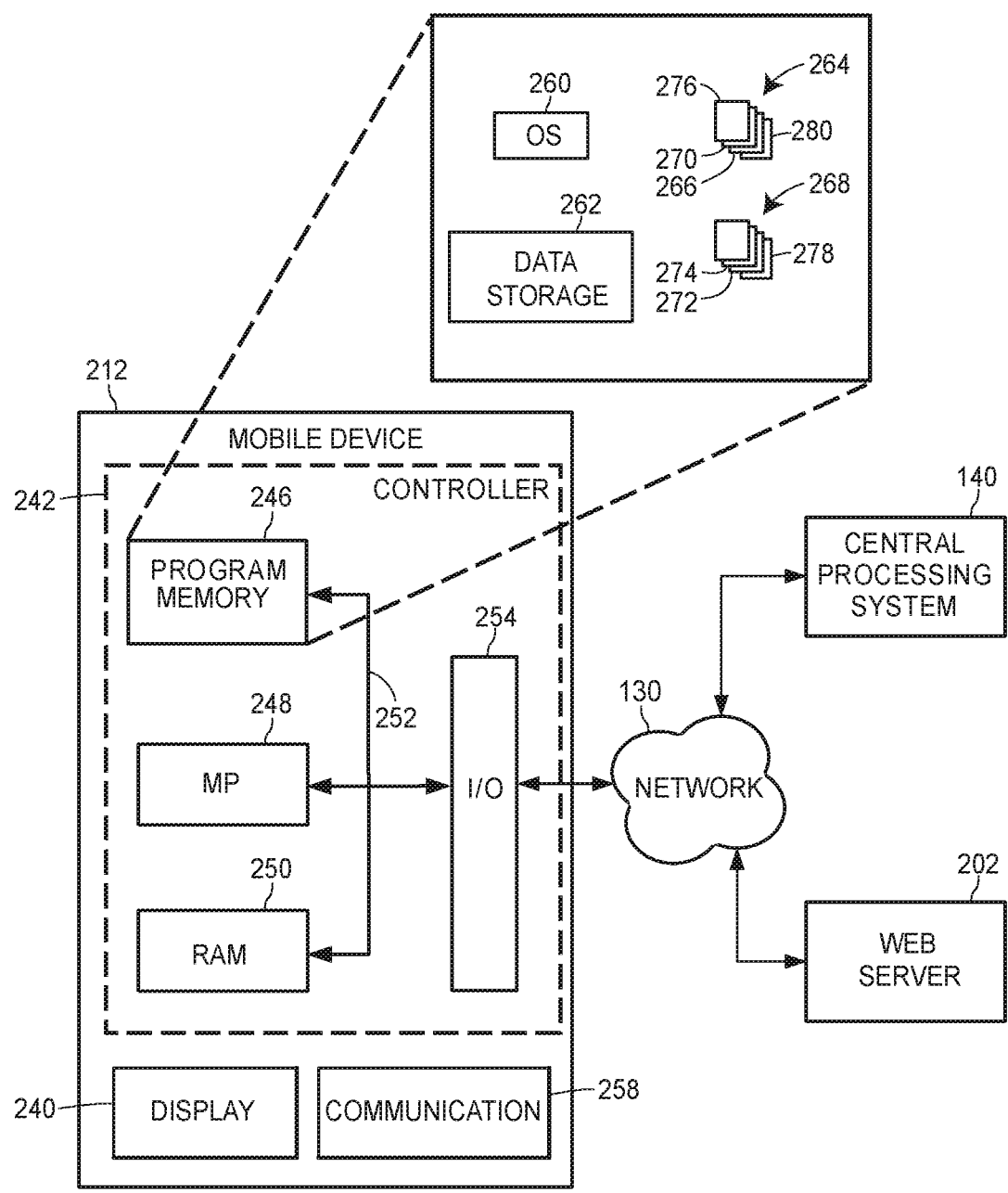
FIG. 1D illustrates a block diagram of an exemplary mobile device.

Referring now to FIG. 1D, the mobile device 212 (or any of the client devices 206-216) includes a display 240, a communication unit 258, a user-input device (not shown), and, like the server 202, a controller 242. Similar to the controllers 155 and 224, the controller 242 includes a program memory 246, one or more microcontroller or a microprocessor (MP) 248, a random-access memory (RAM) 250, and an input/output (I/O) circuit 254, all of which are interconnected via an address/data bus 252. The program memory 246 includes an operating system 260, a data storage 262, and a plurality of software applications 264. The operating system 260, for example, may include one of a plurality of mobile platforms such as the iOS®, Android™, Palm® webOS, Windows Mobile/Phone, BlackBerry® OS, or Symbian® OS mobile technology platforms, developed by Apple Inc., Google Inc., Palm Inc. (now Hewlett-Packard Company), Microsoft Corporation, Research in Motion (RIM), and Nokia, respectively. The data storage 262 may include data such as user profiles, application data for the plurality of applications 264, and other data necessary to interact with the server 202, the facility servers 126, or the server applications 113 through the digital network 130. In some embodiments, the controller 242 may also include, or otherwise be communicatively connected to, other data storage mechanisms (e.g., one or more hard disk drives, optical storage drives, solid state storage devices, etc.) that reside within the mobile device 212.

The communication unit 258 may communicate with the server 202 via any suitable wireless communication protocol network, such as a wireless telephony network (e.g., GSM, CDMA, LTE, etc.), a Wi-Fi network (802.11 standards), a WiMAX network, a Bluetooth network, etc. The user-input device (not shown) may include a "soft" keyboard that is displayed on the display 240 of the mobile device 212, an external hardware keyboard communicating via a wired or a wireless connection (e.g., a Bluetooth keyboard), an external mouse, or any other suitable user-input device. As discussed with reference to the controllers 155 and 224, it should be appreciated that although FIG. 1D depicts only one microprocessor 248, the controller 242 may include multiple microprocessors 248. Similarly, the memory of the controller 242 may include multiple RAMs 250 and multiple program memories 246. Although the FIG. 1D depicts the I/O circuit 254 as a single block, the I/O circuit 254 may include a number of different types of I/O circuits. The controller 242 may implement the RAM(s) 250 and the program memories 246 as semiconductor memories, magnetically readable memories, and/or optically readable memories, for example.

The one or more processors 248 may be adapted and configured to execute any one or more of the plurality of software applications 264 residing in the program memory 242, in addition to other software applications. One of the plurality of applications 264 may be a virtual calendar application 266 that may be implemented as a series of machine-readable instructions for performing the various tasks associated with receiving information at, displaying information on, and transmitting information from the mobile device 212. The virtual calendar application 266 may display a virtual calendar with calendar events associated with various dates on the calendar. For example, the virtual calendar application 266 may be Google Calendar™ Microsoft Outlook®, Yahoo Calendar™, Apple's iCal®, or any other suitable virtual calendar applications. In some embodiments, the virtual calendar application 266 may be associated with and/or embedded in a mail application (not shown) that stores an email inbox in the data storage 262 that stores and indexes received and sent emails, including emails with calendar events. One of the plurality of applications 264 may be a native web browser 270, such as Apple's Safari®, Google Android™ mobile web browser, Microsoft Internet Explorer® for Mobile, Opera Mobile™, that may be implemented as a series of machine-readable instructions for receiving, interpreting, and displaying web page information from the server 202, the facility servers 126, or the server applications 113 while also receiving inputs from the user.

Preferably, a customer, a patient, or a user may launch the virtual calendar application 266 from a client device, such as one of the client devices 206-216, to access the server 202 cooperating with the central processing system 140 and the pharmacies 112 to implement the prescription refill system 100. Additionally, the customer, the patient, or the user may also launch or instantiate any other suitable user interface application (e.g., the native web browser 270, or any other one of the plurality of software applications 264) to access the server 202, the facility servers 126, or the server applications 113 to realize the prescription refill system 100. As used herein, the term "customer" indicates someone purchasing a retail product but may additionally be, by way of example, a patient (i.e., the person named on the prescription), a guardian (e.g., the parent of a child named on the prescription), a care-giver (i.e., anyone who takes care of a patient or picks up the medication on the patient's behalf), or any other person authorized to pick up the prescription on the patient's behalf (also referred to herein as an "authorized user"). Moreover, the term "customer" is not limited to a single person, but may instead be any person or persons having a reason or desire to purchase one or more retail products or to perform one or more functions relating to prescription medications, whether the prescriptions are related to a single patient or multiple patients. For example, a customer could be a caregiver responsible for patients with a specific disease that progresses in a known manner. The caregiver customer might greatly benefit from gaining information related to various medications and health products to assist in his or her caregiver responsibilities. In any event, while the term "customer" may be used interchangeably with the term "patient," in this specification the term "customer" is used primarily so as to avoid confusion. Generally, the term "user" is used when referring to a person who is operating one of the client devices 206-216 and is not exclusive of the terms "customer" and "patient."

As described above, one or both of the databases 146 and 239, illustrated in FIGS. 1A and 1B, respectively, include various information about the pharmacy's customers and the prescriptions filled by the pharmacy, as well as basic biographical information about the customer, such as a customer name, a customer identifier (e.g., an email address of the customer, a customer phone number, etc.), a customer address, an insurance carrier associated with the customer, an insurance group number for the customer, an insurance ID number for the customer, a customer birth date, a health history or condition, customer purchase history, etc. The various information about a customer and prescriptions filled by the pharmacy for the customer may be stored in a user profile.

The purchase history may include data related to purchases the customer routinely makes or has made at the pharmacies 110. The purchase history data may include any product sold by the pharmacies 110 and purchased by a customer, whether in person or online. Where purchases are made by the customer in the store, the purchase data made be linked to the customer record though credit card, an in-store savings card, or other type of point-of-sale identification. Where the purchases are made by the customer over the network 130 or online, the purchases may be linked to the customer through a user profile that is accessible by the customer through the web-enabled device 206-216, as herein described. Additionally, the user profile may include other information such as credit card information or other payment information, one or more customer email addresses, user name and/or password information, online security question/answer information, etc. The user profile may also include other, more or less information than that described above.

User profiles, including a customer's prescription order records, are among the exemplary data that the prescription refill system 100 may store on the databases 146 and 239. The user profile also includes prescription data for each prescription filled by the pharmacy for the customer. The prescription data generally includes, but is not limited to: a name of the medication or drug; an indication whether a generic may be substituted; a dose (e.g., pills per day) of the medication; a number of days of medication to be dispensed (also referred to herein as a "day supply" or a "prescribed day supply"); a number of refills prescribed; a number of refills remaining; a prescription date; a prescribing physician; a phone number for the prescribing physician; a date on which the prescription was most recently adjudicated; a calculated date on which the prescription may next be adjudicated for the prescription; a remaining day supply for the prescription; a percent-consumption period indicating the number of days it would take to consume the required minimum percent-fill consumed of the fill for the prescription); and a prescription number. Of course, the prescription data need not include all of the information above, such as when the prescription refill system 100 determines some information (e.g., the next adjudication date) but does not store it, or stores it some place other than with the prescription data in the database 146 or the database 239. Moreover, the prescription data may include additional information not mentioned above.

In any event, the prescription refill system 100 may perform various tasks, such as sending a calendar event that includes one or more refill-eligible prescriptions to a customer when the customer's one or more prescriptions are eligible for refill. In response to receiving the calendar event, the customer may place a refill order for one or more refill-eligible prescriptions by solely replying to the received calendar event directly via the virtual calendar application 266. In other embodiments, the customer may reply to the received calendar event via the mail application (not shown) or a combination of the virtual calendar application 266 and the mail application. For example, in some scenarios, the virtual calendar application 266 may be embedded within the mail application (not shown).

In generating the calendar event, for example, the server 202 or the central processing system 140 may query the databases 146 and 239 to obtain prescription data from the user profiles to determine, for a given customer, whether one or more prescriptions are eligible for refill on a particular date. For each prescription, the system 100 may use any type of stored prescription data, such as the number of refills remaining, the remaining day supply for the prescription, order records, etc., from the user profiles to determine whether a particular prescription is eligible for refill on a particular date. After this determination, the system 100 may group the refill-eligible prescriptions together on a per customer (or per customer family, etc.) basis to more efficiently remind the customer that multiple prescriptions are eligible for refill. Additionally, the system 100 may generate and assign a refill reminder identifier (described below) to the one or more refill-eligible prescriptions for the particular date and also associate the refill reminder identifier with a customer identifier from the user profile, such as the customer's email address or phone number. The system 100 may then store the newly generated refill reminder identifier within a database of refill reminder identifiers (e.g., one of the databases 140, 239). In generating a calendar event (described below), for example, the system 100 preferably may insert the newly assigned refill reminder identifier into the subject line of the calendar event so that when the customer replies to the calendar event, the refill reminder identifier will be easily extracted by the system 100 parsing the text of the subject line. Furthermore, the system 100 may also include the customer's biographical information, the prescription numbers preferably masked for privacy reasons, the pharmacy (and the information of the pharmacy) associated with the one or more refill-eligible prescriptions (e.g., the pharmacy location where the one or more prescriptions were last filled, etc.), or any other desired information in the refill reminder email. The server 202 may send, using the customer's email address or phone number, this newly generated calendar event to the customer to alert the customer that one or more prescriptions are eligible for refill on the particular date.

Figure 2:
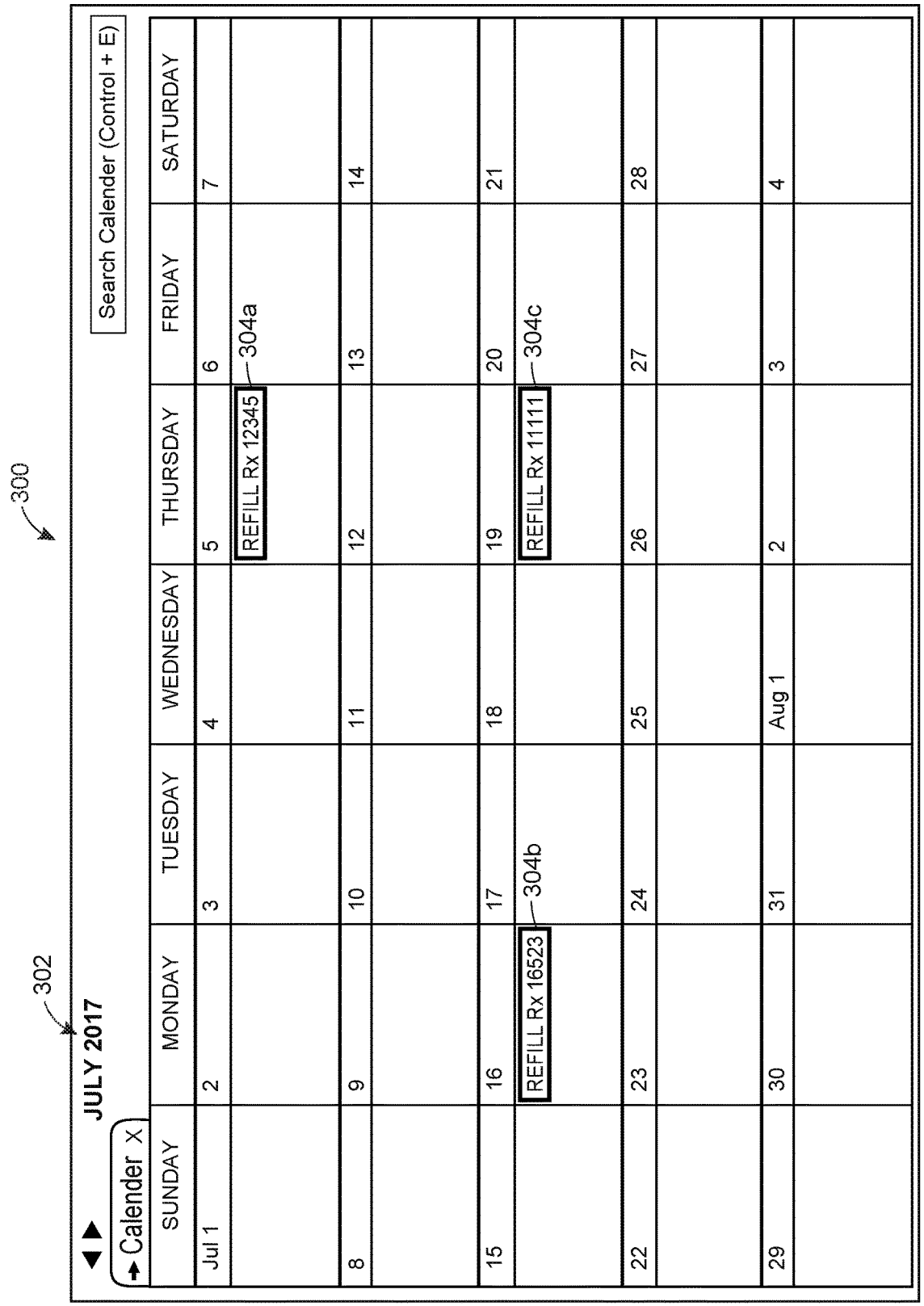
FIG. 2 depicts an exemplary calendar screen of a virtual calendar including refill reminders transmitted by the server of FIG. 1C.

As shown in FIG. 1B, to access the server 202, the facility servers 126, or the server applications 113, the user may execute the virtual calendar application 266 or the web browser 270 on one of the client devices 206-216, such as the mobile device 212. Using the virtual calendar application 266, for instance, the user may request to view any calendar events, such as the calendar event described above, or other electronic messages transmitted by the server 202 to the mobile device 212. In any event, the user may launch the virtual calendar application 266 from one of the client devices 206-216 via any suitable manner, such as touch-selecting a virtual calendar application icon (not shown) on the display 240 of the mobile device 212, double-clicking on the virtual calendar application icon via a mouse of a computer 216 or a trackpad (not shown) of a laptop 214. In other scenarios, such as when the virtual calendar application 266 is embedded within a mail application (not shown), the user may launch the virtual calendar application 266 from one of the client device 206-216 by touch-selecting or double-clicking on a mail application icon. In any event, after the user launches the virtual calendar application 266, a calendar screen 300 as shown in FIG. 2 of the virtual calendar application 266 is displayed to the user on the mobile device 212. The user may navigate and may select a particular calendar event (described below) within the calendar screen 300.

With reference now to FIG. 2, the calendar screen 300 is displayed to a user via the virtual calendar application 266 of a client device, such as the mobile device 212, a smartphone, a tablet, a laptop, or any other client device 206-216.

The calendar screen 300 may include a monthly calendar view, such as July 2017 (ref. no. 302), a yearly calendar view, a weekly calendar view, a daily calendar view, etc. displaying one or several dates within the time frame of the view (e.g., Jul. 1, 2017-Jul. 31, 2017). Each date in the calendar screen 300 may include an indicator 304a-c of the customer's prescriptions eligible to be refilled on the particular date. Dates on which the customer is not eligible to refill prescriptions may be left blank. In some embodiments, each indicator 304a-c may also be provided with a specific time at which the corresponding prescriptions are eligible for refill (e.g., 3 p.m.). In any event, the indicators 304a-c may include a description of the refill reminder, such as "Refill Rx 12345" which includes the refill reminder identifier "12345." The indicators 304a-c may also include user controls, which when selected by the user, display a calendar event for refilling prescriptions on the selected date. For example, when the user selects the indicator 304a "Refill Rx 12345," the virtual calendar application displays a calendar event 222 as shown in FIG. 3, which allows the user to refill prescriptions on Jul. 5, 2017 corresponding to refill reminder identifier "12345."

Figure 3:
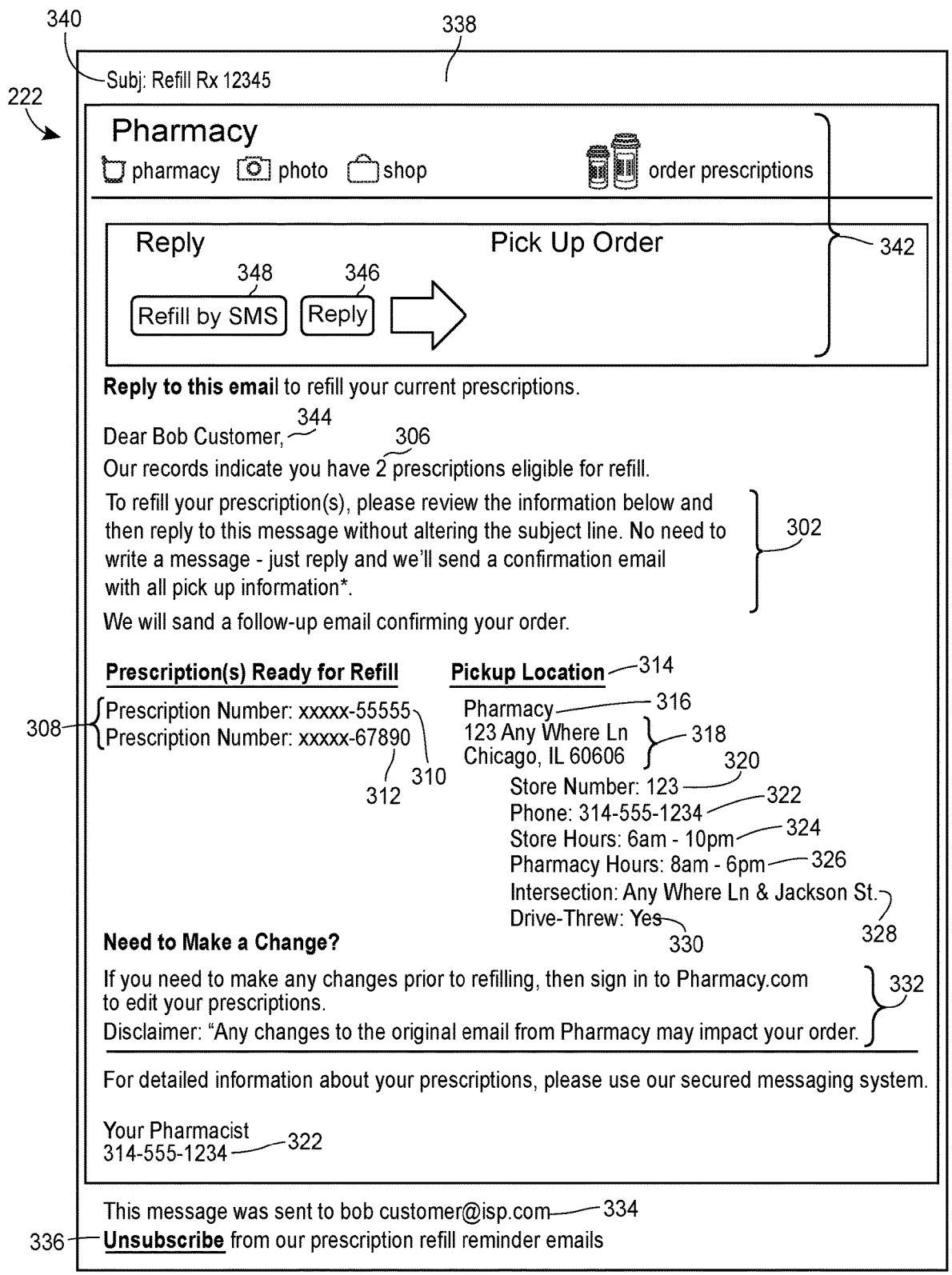
FIG. 3 depicts an exemplary calendar event transmitted by the server of FIG. 1C.

With reference now to FIG. 3, a calendar event 222 of the virtual calendar application 266 is displayed to a user on a client device, such as the mobile device 212, a smartphone, a tablet, a laptop, or any other client device 206-216. The calendar event 222 may include a banner 342 that conveys the pharmacy's name, the types of services the pharmacy offers, directions in using the prescription refill system 100, advertisements, etc. Moreover, the calendar event 222 may include a name of the customer 344, a number count of prescriptions 306 associated with the customer that are eligible for refill on the particular date, and a listing of the prescription numbers 308. Each individual prescription number 310, 312 in the listing of the prescription numbers 308 corresponds to a particular prescription medication or drug associated with the customer that is eligible for refill on the particular date. Each prescription number 310, 312 may be masked or partially hidden to protect the privacy of the customer in case the email is incorrectly sent to someone other than the customer. For example, the prescription number 310 is labeled as "XXXXX-55555" in FIG. 3 so that only the last five digits are exposed and the first five digits remain undisclosed. However, the customer may still identify and verify each prescription number 310, 312 via the last five digits. In other embodiments, the customer may consent to allowing the prescription refill system 100 to display the name of each prescription medication or drug. For example, the customer may select a user control that indicates that the customer consents to transmitting the name of each prescription medication or drug. In response to receiving the customer's consent, the calendar event 222 may include the name of each prescription medication or drug along with a respective masked or partially hidden prescription number.

As illustrated in FIG. 3, the calendar event 222 may also include a pickup location 314 where the customer may physically retrieve her refilled prescriptions. Generally, the pickup location 314 is the pharmacy where the customer last picked up her prescriptions, but the pickup location may include any pharmacy that is determined in any manner. The pickup location 314, for example, may include a pharmacy name 316, a pharmacy address 318, a pharmacy phone number 320, store hours for the pharmacy 324, pharmacy hours for the pharmacy 326, a nearby intersection to the location of the pharmacy 328, and an indicator 330 of whether the pharmacy includes a drive through. The calendar event 222 may include instructions 332 that allow the customer to edit any of the prescription information or pickup location information if the information is incorrect. For example, the instructions 332 may include a hyperlink that, in response to being selected, directs the customer to a log in web page (not shown) that allows the customer to interact with the system 100 to edit any incorrect information. The calendar event 222 may also include an identity notification 334 that allows the customer to verify that the calendar event 222 is intended for the customer via the email or phone number of the customer for example. Moreover, if the customer desires to no longer receive calendar events 222 from the prescription refill system 100, the customer may select an unsubscribe link 336 to opt out of the calendar service.

Importantly, a subject line 340 of the calendar event 222 includes a refill reminder identifier 338 that associates the listing of the prescription numbers 308 and the customer's email address 334 or phone number. For example, in FIG. 3, the refill reminder identifier 338 appears in the subject line 340 as "12345" and is used by the prescription refill system 100 to assist in tracking the refill transactions or orders associated with the customer and the refill-eligible prescriptions 310, 312 of the listing of prescription numbers 308.

In any event, after receiving the calendar event 222, the customer may review and verify the email address 334, the listing of prescription numbers 308, and the pharmacy information 316-330 associated with the pickup location 314 within the calendar event 222. When the customer is satisfied that the above information is correct and desires to place a refill order for the listing of prescriptions 308, the customer may select a reply user control 346 within the virtual calendar application 266, the mail application, or within the web browser 270 to respond to the calendar event 222. By selecting the reply user control 346, the virtual calendar application 266, mail application, or web browser 270 generates a reply electronic communication (not shown) addressed to a reply email address or phone number that preferably identifies the server 202. Advantageously, the newly generated reply electronic communication includes the entire content of the subject line 340 of the received calendar reminder (including the refill reminder identifier) in addition to the indicator "Re:" that signifies that the email is a reply electronic message. For example, the subject line 340 of the received calendar event 222 recites "Refill Rx—12345". When the customer replies to the calendar event 222, the newly generated reply electronic communication recites "Re: Refill Rx—12345" and allows the server 202 to authenticate and to process the incoming reply electronic communication for refill at the appropriate pharmacy.

In other embodiments, the customer may place a refill order for the listing of prescriptions by sending an SMS text message or any other communication to an email address or phone number indicated in the calendar event 222 that identifies the server 202. For example, the customer may send an SMS text message to a phone number indicated in the calendar event 222 with the refill reminder identifier included in the body of the message. More specifically, the customer may select the "Refill by SMS" user control 348 within the virtual calendar application 266, the mail application, or within the web browser 270 to respond to the calendar event 222. By selecting the "Refill by SMS" user control 348, the virtual calendar application 266, mail application, or web browser 270 causes the customer's client device 206-216 to open a messaging application. For example, the messaging application may provide an application programming interface (API) for accessing the messaging application. The virtual calendar application 266, mail application, or web browser 270 may invoke the API to launch the messaging application and auto-populate an SMS message.

For example, the virtual calendar application 266, mail application, or web browser 270 may auto-populate an SMS message in the messaging application to include the phone number indicated in the calendar event that is associated with the server 202. The body of the SMS message may be auto-populated with the term "Refill" and the refill reminder identifier 338. By selecting a "Send" button in the messaging application, the server 202 may receive the refill order. In some embodiments, the "Refill by SMS" user control 348 is only included in the calendar event 222 when the customer's client device 206-216 is a smart phone, a tablet computer, an internet-enabled cell phone, a PDA, or other device for communicating over a cellular network. When the customer's client device 206-216 is a desktop computer for example, the "Refill by SMS" user control 348 is not included.

In any event, to provide calendar events to the customer's client device 206-216, the server 202 may generate a virtual calendar specific to the customer having a calendar identifier (calendar ID). For each date that the customer is eligible for a refill on one or more prescriptions the server 202 may add a calendar event for the date including a refill reminder identifier that corresponds to the prescriptions eligible for refill on the date. In some embodiments, a calendar event may be generated each time a new prescription having a refill date is added to the customer's user profile. In other embodiments, a calendar event may be generated within a threshold time period of the refill date (e.g., one month, two weeks, one week, etc.) to allow for multiple prescriptions to be eligible for refill on the date before generating the calendar event. In any event, the server 202 may generate a calendar subscription link which allows the customer to subscribe to the virtual calendar. For example, the calendar subscription link may be an iCalendar feed or Rich Site Summary (RSS) feed. The calendar subscription link may be provided to the customer's client device 206-216 and more specifically to the customer's virtual calendar application 266 or mail application, via a customer identifier such as an email address or phone number. The customer may be presented with the option to subscribe to the virtual calendar specific to the customer, thereby authorizing the server 202 to communicate the virtual calendar to the customer's client device 206-216 via the iCalendar or RSS feed. In some embodiments, the virtual calendar application 266 may store the calendar ID to authorize subsequent communications from the virtual calendar specific to the customer to be displayed on the client device 206-216.

When the customer subscribes, the client device 206-216 may provide a notification to the server 202 indicating the customer has subscribed to the virtual calendar. The client device 206-216 may then obtain calendar events from the virtual calendar via the iCalendar or RSS feed. In this manner, when a calendar event is generated for the virtual calendar, the customer's virtual calendar application is updated in real-time or at least near real-time to include the calendar event. For example, the server 202 may determine on Jun. 5, 2017 that the current date is within a threshold time period of Jul. 5, 2017 (one month). Accordingly, the server 202 may obtain prescription information for each prescription in the customer's user profile having a refill date of Jul. 5, 2017. Then the server 202 may assign a refill reminder identifier to the prescriptions in the customer's user profile having a Jul. 5, 2017 refill date and store the refill reminder identifier in association with the corresponding prescriptions in the database 146, 239. Additionally, the server 202 may generate a calendar event for the virtual calendar specific to the customer and the calendar event may include a refill reminder identifier and a date of Jul. 5, 2017. When the calendar event is added to the virtual calendar, the virtual calendar application of the customer's client device 206-216 may receive the calendar event via the iCalendar or RSS feed. In some embodiments, a calendar event may be generated in an ICS file or any other suitable format supported by virtual calendar applications such as Google Calendar™, Microsoft Outlook®, Yahoo Calendar™, or Apple's iCal®.

Also in some embodiments, the calendar event may also include one or several reminders, each within a threshold time period of the refill date. For example, the virtual calendar application may display an alert one hour before 9 a.m. on the refill date so that the customer remembers to order a refill before going to work. In another example, the virtual calendar application may display three alerts, one 24 hours before 9 a.m. on the refill date, another alert one hour before 9 a.m., and a third alert a half hour before 9 a.m.

In an exemplary scenario, customer John Doe has three prescription medications eligible for refill on Dec. 20, 2019. He receives a calendar event that is saved in his Microsoft Outlook® calendar and includes a refill reminder identifier that may be used as a reference to the three prescription medications. On or around Dec. 20, 2019, John may click or touch-select the calendar event and may be prompted with an option to reply to the calendar event to order the corresponding prescription refills. By selecting a reply user control, John's client device 206-216 may transmit a reply electronic communication to the server 202 that includes the refill reminder identifier (e.g., in the subject line of the reply electronic communication) and a customer identifier (e.g., in the "from" field of the rely electronic communication). Accordingly, the server 202 may retrieve prescription numbers corresponding to the refill reminder identifier from the database 146, 239 and transmit a refill order to John Doe's designated pharmacy 112. Then John may go to the pharmacy 112 to pick up the three prescription medications.

Figure 4:
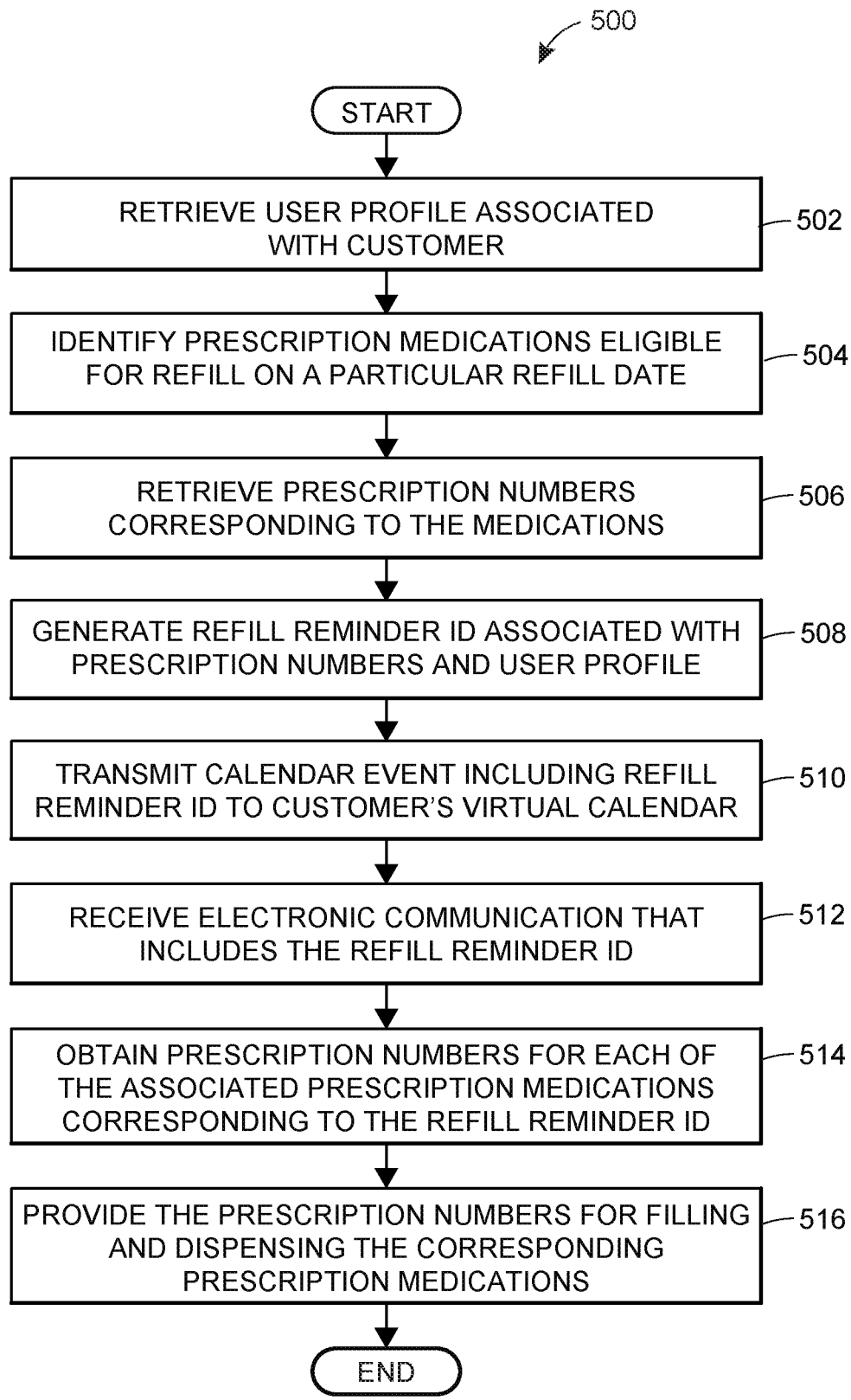
FIG. 4 illustrates an exemplary method implementing the prescription refill system in accordance with the presently described embodiments.

FIG. 4 depicts a flow diagram of an exemplary method 500 for providing a refill order via a calendar reminder. The method 500 may be executed on the server 202. In some embodiments, the method 500 may be implemented in a set of instructions stored on a non-transitory computer-readable memory and executable on one or more processors of the server 202. For example, the method 500 may be performed by the server application 238 as shown in FIG. 1C. In other embodiments, the method 500 may be implemented by the central processing system 140 or a combination of these devices.

At block 502, the server 202 may retrieve a user profile associated with a customer from a database 146, 239. More specifically, the server 202 may use a customer identifier (e.g., an email address, phone number, etc.) to obtain Bob Customer's user profile, for example.

Then at block 504, the server 202 may identify prescription medications or drugs corresponding to the customer and eligible for refill on a particular date. For example, the server 202 may identify prescription medications or drugs corresponding to Bob Customer and eligible for refill on Jul. 5, 2017. To identify the prescription medications eligible for refill, the server 202 may retrieve prescription data within Bob's user profile from the database 146, 239. More specifically, the server 202 may identify prescription medications from Bob's user profile having a refill date matching the particular date.

As mentioned above, for each prescription medication in the database 146, 239, the user profile may include a name of the medication or drug; an indication whether a generic may be substituted; a dose (e.g., pills per day) of the medication; a number of days of medication to be dispensed (also referred to herein as a "day supply" or a "prescribed day supply"); a number of refills prescribed; a number of refills remaining; a prescription date; a prescribing physician; a phone number for the prescribing physician; a date on which the prescription was most recently adjudicated; a calculated date on which the prescription may next be adjudicated for the prescription; a remaining day supply for the prescription; a percent-consumption period indicating the number of days it would take to consume the required minimum percent-fill consumed of the fill for the prescription); and a prescription number.

At block 506, the server 202 may retrieve a prescription number from the user profile corresponding to each of the identified prescription medications. Then a refill reminder identifier may be generated that is associated with each of the retrieved prescription numbers and user profile and stored in the database 146, 239 (block 508). In this manner, the refill reminder identifier may later be used to retrieve the corresponding prescription numbers for dispensing and filling prescription medications for the customer. Additionally, the refill reminder identifier may also be used to verify that the associated user profile corresponds to the customer requesting the refill (e.g., by comparing the customer identifier from the user profile associated with the refill reminder identifier to a customer identifier included in a reply electronic communication).

The server 202 may generate a calendar event for the particular date that includes the refill reminder identifier (e.g., in the subject line, description, or other portion of the calendar event). In some embodiments, the server 202 may generate a virtual calendar specific to the customer having a calendar ID. Then the server 202 may generate and transmit a calendar subscription link to the customer's client device 206-216 via a customer identifier such as an email address or phone number. The customer may be presented with the option to subscribe to the virtual calendar specific to the customer, and when the customer subscribes, the server 202 may transmit a calendar event for the particular date that includes the refill reminder identifier (block 510).

In some embodiments, the calendar event may also include the name of the pharmacy filling the prescription medications, the name of the customer, a number count of prescriptions eligible for refill on the particular date, a listing of masked or partially hidden prescription numbers, a pickup location for retrieving the refilled prescriptions, etc. as in the calendar event 222 as shown in FIG. 3. If the customer consents to allowing the name of each prescription medication or drug to be displayed, the calendar event may also include the name of each prescription medication or drug.

In response to receiving the calendar event, the customer may select a reply user control to respond to the calendar event. By selecting the reply user control, the server 202 may receive a reply electronic communication that includes the refill reminder identifier (e.g., in the subject line of the reply electronic communication) and a customer identifier (e.g., the email address of the customer sending the reply electronic communication) (block 512).

After the server 202 validates the refill reminder identifier by verifying that that the refill reminder identifier exists in a database of refill reminder identifiers and validates the customer identifier by verifying that the customer identifier exists in a database of customer identifiers, the server 202 obtains indicators of each of the prescription medications or drugs (e.g., prescription numbers) associated with the refill reminder identifier from the one or more databases 146, 239 (block 514). The server 202 may then provide the indicators (e.g., prescription numbers) to the appropriate pharmacy 112 for filling and dispensing the corresponding prescription medications (block 516). In some embodiments, the server 202 may generate a refill order number associated with the refill reminder identifier and transmit the refill order number to the appropriate pharmacy 112 along with the prescription numbers. Additionally, the server 202 may receive an order confirmation from the pharmacy 112, and in turn may transmit, to the customer, a refill order confirmation electronic communication that makes the customer aware of the refill order confirmation.

Figure 5:
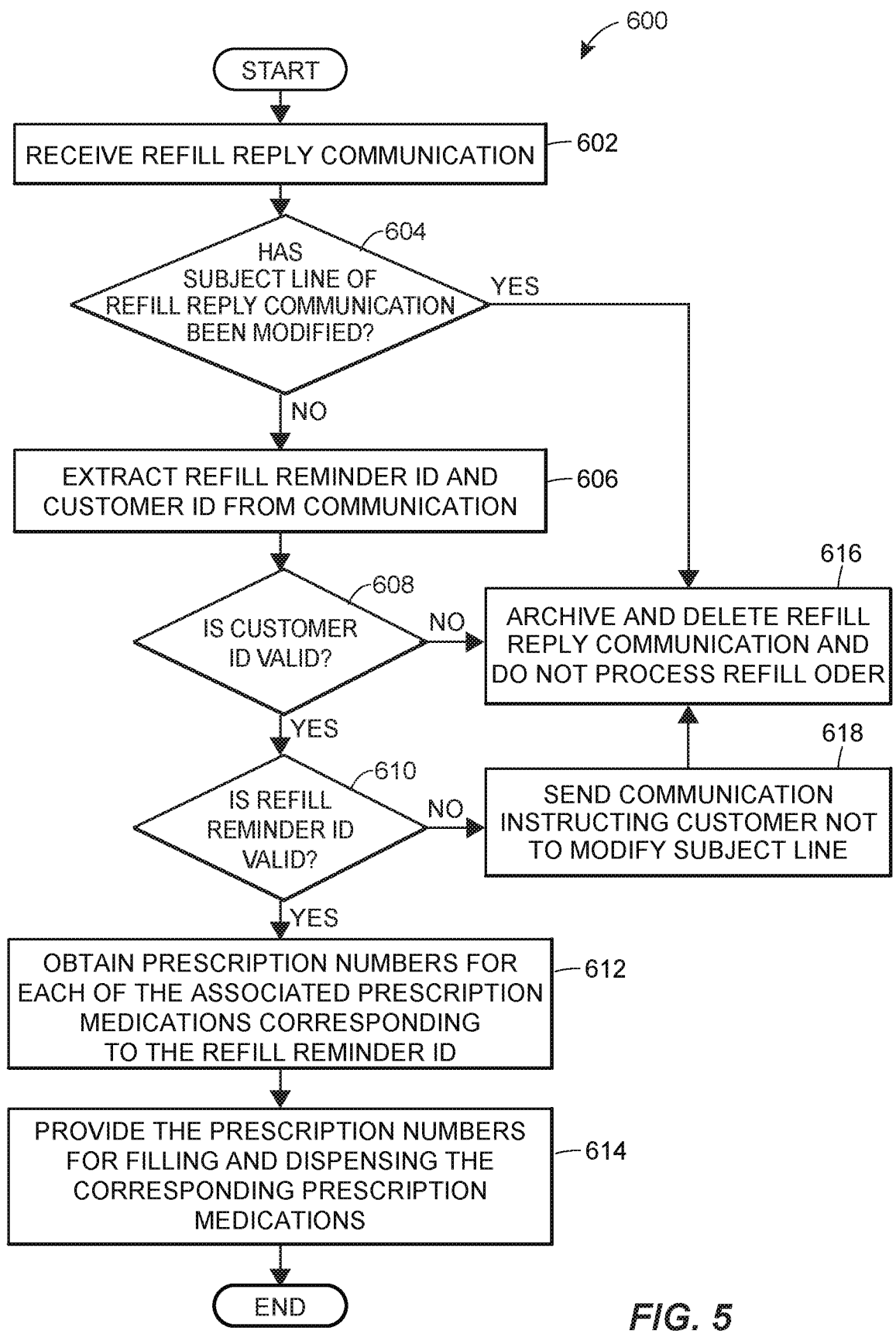
FIG. 5 illustrates an exemplary detailed method implementing the prescription refill system in accordance with the presently described embodiments.

The method 600 illustrated in FIG. 5 provides additional detail regarding the method 500. In one of the various manners described above, a customer may communicate with the server 202 by, for example, replying to the calendar event 222 via the virtual calendar application 266, mail application, or the web browser 270. Alternatively, the customer may communicate with the server 202 via an SMS text message, instant message, or in any other suitable manner.

In any event, upon receiving a refill reply electronic communication, such as an email, that is in reply to a calendar event (block 602), the server 202 retrieves the received refill reply email from the email inbox (not shown) stored in the database 146, 239. Because of the high volume of refill reply emails, the server 202 may also retrieve groups of emails in batches from the inbox at periodic intervals as opposed to retrieving each email individually. For example, the server 202 may retrieve a batch of 5,000 emails every ten minutes from the inbox to assist the system 100 in better processing the incoming refill reply emails. Of course, the number of emails retrieved in each batch and the periodic time intervals may be any amount.

After retrieving the refill reply email from the email inbox, the server 202 may determine whether the text in the subject line 340 has been modified except for an added reply message indicator (e.g., the added term "Re:" in a subject line 340 of an email specifies that the received email is in response to another email) (block 604). The server 202 preferably may be implemented to recognize specific phrases of text while ignoring the phrase "Re:" to assist in determining whether the subject line 340 of the retrieved email has been modified. This initial determination of whether the subject line 340 has been modified may assist in filtering out automatic reply emails (e.g., an "Out of Office" reply email, a "On Vacation" email, etc.) or unsolicited "spam" emails. For example, if the server 202 retrieves an email that includes a term "AutoReply" or a term "Out of Office" that has been added to the subject line 340, one may assume that an automated system automatically sent the email rather than a human sending the email. In any event, if the server 202 determines that an automatic reply email has been sent, the server 202 may archive the email, may delete the email from the inbox, and/or may not process the refill order (block 616).

If server 202 determines that the subject line 340 of the retrieved email has not been modified except for the added reply message indicator, then the server 202 extracts the refill reminder identifier 338 from the subject line 340 and an email address (e.g., customer identifier) from a "from" field in the email, respectively (block 606).

After the extraction of the refill reminder identifier 338 and the customer identifier, the server 202 may proceed to validate the customer identifier (block 608). In various embodiments, the server 202 may check the length of the customer identifier (e.g., to determine whether it is the correct length), determine whether the customer identifier includes any unacceptable characters (e.g., special characters, non-numeric characters, etc.), and/or determine whether the customer identifier includes a delimiter (e.g., a hyphen or a space). Validation of the customer identifier may also include validating the customer identifier against a database of customer identifiers (e.g., in one of the databases 146, 239).

In addition to determining whether the customer identifier exists in a database of customer identifiers, the server 202 may also determine whether the customer identifier corresponds to a customer authorized to refill the prescriptions medications associated with the refill reminder identifier. For example, the refill reminder identifier may be associated with a customer identifier from the user profile of the customer eligible to refill the prescriptions. The customer identifier associated with the refill reminder identifier may be compared to the customer identifier for example, from the "from" field in the refill reply electronic communication. When there is a match, the customer identifier may be validated.

In any event, if the server 202 determines that the customer identifier is invalid (block 608), the server 202 may archive the refill reply email, may delete the refill reply email, and/or may not process the refill order (block 616). If the server 202 determines that the customer identifier is valid, the server 202 proceeds to determine whether the extracted refill reminder identifier 338 is valid (block 610).

Validation of the refill reminder identifier 338 may include similar processes or steps as to the customer identifier validation process described above including checking the length of the refill reminder identifier 338, determining whether the refill reminder identifier 338 includes any unacceptable characters, validating the customer identifier 334 against a database of refill reminder identifiers, and/or determining whether the refill reminder identifier 338 includes a delimiter (e.g., a hyphen or a space). If the server 202 determines that the refill reminder identifier 338 is invalid, the server 202 may transmit a new electronic communication that instructs the customer to resend a reply to the calendar event 222 without modifying the subject line 340 (block 618). The server 202 may then archive the refill reply email, may delete the refill reply email, and/or may not process the refill order (block 616). However, if the server 202 determines that the refill reminder identifier 338 is valid, the server 202 proceeds to determine whether a previously generated refill order number (not shown) associated with the refill reminder identifier 338 exists in the order number database (e.g., in one of the databases 146, 239).

Using the refill reminder identifier 338, the server 202 may determine whether a previously generated refill order number that is associated with the refill reminder identifier 338 exists in a database of refill order numbers. A refill order number is generated at the time of placing a prescription fill order and is associated with a specific refill reminder identifier 338. In querying the database of order numbers for a refill order number that is associated with a specific refill reminder identifier 338, the server 202 may verify the previous placement of a refill order. This verification prevents the server 202 from placing duplicate refill orders because the refill reminder identifier 338 may only be associated with one refill order number. If the server 202 determines that a refill order number exists in the database of order numbers, the server 202 may then not process the already processed order and may archive and then delete the refill reply email (block 616). If, however, the system 100 determines that no related refill order numbers exist in the order number database, the system 100 proceeds to generate a new refill order number that is associated with the refill reminder identifier 338.

The server 202 may store the newly generated refill order number and associate the refill order number with the refill reminder identifier 338. Using the refill reminder identifier 338, the server 202 may then obtain one or more prescription numbers 310, 312 that are associated with the extracted refill reminder identifier 338 from a database of prescription numbers (e.g., in one of the databases 146, 239) (block 612). Additionally, the system 100 may retrieve the pharmacy name 316 associated with the extracted refill reminder identifier 338 from a database of pharmacy information (e.g., in one of the databases 146, 239). After determining the pharmacy 112 and one or more prescription numbers associated with the extracted refill reminder identifier 338, the server 202 may transmit the newly generated refill order number and the determined one or more prescription numbers to the determined pharmacy 112 for filling and dispensing the prescribed medications (block 614). The pharmacy 112, in response, may transmit a confirmation that the refill order number and one or more prescription numbers are safely received and that the refill order is placed. In response to receiving this confirmation, the server 202 may transmit a refill order confirmation email to the customer that may include a confirmation that the refill order was placed, a status of the refill order, a date, a time, and pharmacy information.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

We claim:

1. A method of providing a refill order via a calendar reminder, the method executed by one or more processors programmed to perform the method, the method comprising:
   identifying, by one or more processors, one or more prescription drugs eligible for refill for a user on a particular refill date;
   generating, by the one or more processors, a refill reminder identifier associated with the one or more prescription drugs for uniquely identifying each of the one or more prescription drugs;
   transmitting, by the one or more processors to a client device of the user, a calendar event to be displayed on a virtual calendar of the client device on the particular refill date, the calendar event including the refill reminder identifier;
   in response to transmitting the refill reminder identifier to the client device, receiving, at the one or more processors, an electronic communication from the virtual calendar of the user, the electronic communication including the refill reminder identifier;
   in response to receiving the electronic communication, obtaining, by the one or more processors, an indicator for each of the one or more prescription drugs corresponding to the refill reminder identifier; and
   providing, by the one or more processors, the indicators for filling and dispensing the one or more prescription drugs to the user.

2. The method of claim 1, further comprising:
   parsing, by the one or more processors, the electronic communication to (i) obtain the refill reminder identifier and (ii) identify whether the electronic communication is generated by the user or by an automated system.

3. The method of claim 2, wherein when the electronic communication is generated by an automated system, an indicator for each of the one or more prescription drugs associated with the refill reminder identifier is not obtained and the electronic communication is removed.

4. The method of claim 1, further comprising:
   determining, by the one or more processors, one or more users authorized to order a refill for the one or more prescriptions drugs; and
   parsing, by the one or more processors, the electronic communication to determine whether the user transmitting the electronic communication is an authorized user.

5. The method of claim 1, wherein the calendar event is compatible with a virtual calendar application on the client device.

6. The method of claim 1, further comprising:
   transmitting, by the one or more processors, a calendar subscription link to the client device; and
   receiving, at the one or more processors from the client device, a confirmation communication indicating the calendar subscription link has been accepted.

7. The method of claim 6, wherein the calendar subscription link is related to a user profile for the user and further comprising:
   storing, by the one or more processors, indications of prescription drugs for the user that are eligible for refill in the user profile;
   for a particular date, obtaining, by the one or more processors from the user profile, a subset of the indications of prescriptions drugs having the particular refill date;
   generating, by the one or more processors, a refill reminder identifier associated with the subset of the indications of prescription drugs; and
   transmitting, by the one or more processors via the calendar subscription link, the calendar event to be displayed on the virtual calendar of the client device, the calendar event including the refill reminder identifier.

8. The method of claim 7, further comprising:
   updating, by the one or more processors, the virtual calendar of the client device with new calendar events for additional prescription drugs having new refill dates.

9. The method of claim 1, wherein the indicator for each of the one or more prescription drugs is a prescription number.

10. The method of claim 1, wherein the calendar event further includes an indication of a pharmacy location at which to pick up the one or more prescription drugs.

11. A system for providing a refill order via a calendar reminder, the system comprising:
    one or more processors;
    a communication network;
    a non-transitory computer-readable memory coupled to the one or more processors, and the communication network, and storing thereon instructions that, when executed by the one or more processors, cause the system to:
       identify one or more prescription drugs eligible for refill for a user on a particular refill date;
       generate a refill reminder identifier associated with the one or more prescription drugs for uniquely identifying each of the one or more prescription drugs;
       transmit, via the communication network to a client device of the user, a calendar event to be displayed on a virtual calendar of the client device on the particular refill date, the calendar event including the refill reminder identifier;
       in response to transmitting the refill reminder identifier to the client device, receive, via the communication network, an electronic communication from the virtual calendar of the user, the electronic communication including the refill reminder identifier;
       in response to receiving the electronic communication, obtain an indicator for each of the one or more prescription drugs corresponding to the refill reminder identifier; and
       provide the indicators for filling and dispensing the one or more prescription drugs to the user.

12. The system of claim 11, wherein the instructions further cause the system to:
    parse the electronic communication to (i) obtain the refill reminder identifier and (ii) identify whether the electronic communication is generated by the user or by an automated system.

13. The system of claim 12, wherein when the electronic communication is generated by an automated system, an indicator for each of the one or more prescription drugs associated with the refill reminder identifier is not obtained and the electronic communication is removed.

14. The system of claim 11, wherein the instructions further cause the system to:
    determine one or more users authorized to order a refill for the one or more prescriptions drugs; and
    parse the electronic communication to determine whether the user transmitting the electronic communication is an authorized user.

15. The system of claim 11, wherein the calendar event is compatible with a virtual calendar application on the client device.

16. The system of claim 11, wherein the instructions further cause the system to:
   transmit, via the communication network, a calendar subscription link to the client device; and
   receive, via the communication network from the client device, a confirmation communication indicating the calendar subscription link has been accepted.

17. The system of claim 16, wherein the calendar subscription link is related to a user profile for the user and the instructions further cause the system to:
   store indications of prescription drugs for the user that are eligible for refill in the user profile;
   for a particular date, obtain, from the user profile, a subset of the indications of prescriptions drugs having the particular refill date;
   generate a refill reminder identifier associated with the subset of the indications of prescription drugs; and
   transmit, via the calendar subscription link, the calendar event to be displayed on the virtual calendar of the client device, the calendar event including the refill reminder identifier.

18. The system of claim 17, wherein the instructions further cause the system to:
   update the virtual calendar of the client device with new calendar events for additional prescription drugs having new refill dates.

19. The system of claim 11, wherein the indicator for each of the one or more prescription drugs is a prescription number.

20. The system of claim 11, wherein the calendar event further includes an indication of a pharmacy location at which to pick up the one or more prescription drugs.

* * * * *